United States Patent
Lai et al.

(10) Patent No.: US 10,702,496 B2
(45) Date of Patent: *Jul. 7, 2020

(54) METHOD OF USING A COMPOSITION FOR ENHANCING NEWBORN INFANT COGNITIVE, BRAIN AND/OR CNS DEVELOPMENT

(71) Applicant: ABBOTT LABORATORIES, Abbott Park, IL (US)

(72) Inventors: Chron-si Lai, Blacklick, OH (US); Matthew Kuchan, Westerville, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/962,545

(22) Filed: Apr. 25, 2018

(65) Prior Publication Data

US 2018/0235930 A1    Aug. 23, 2018

Related U.S. Application Data

(62) Division of application No. 14/771,719, filed as application No. PCT/US2014/025541 on Mar. 13, 2014, now Pat. No. 9,980,939.

(60) Provisional application No. 61/778,974, filed on Mar. 13, 2013.

(51) Int. Cl.

| A61K 31/202 | (2006.01) |
|---|---|
| A61K 31/355 | (2006.01) |
| A61K 47/22 | (2006.01) |
| A61K 9/00 | (2006.01) |
| A61P 3/02 | (2006.01) |
| A23L 33/00 | (2016.01) |
| A23L 33/12 | (2016.01) |
| A23L 33/15 | (2016.01) |

(52) U.S. Cl.
CPC ............ *A61K 31/355* (2013.01); *A23L 33/12* (2016.08); *A23L 33/15* (2016.08); *A23L 33/40* (2016.08); *A61K 9/0095* (2013.01); *A61K 31/202* (2013.01); *A61K 47/22* (2013.01); *A23V 2002/00* (2013.01)

(58) Field of Classification Search
None
See application file for complete search history.

(56) References Cited

U.S. PATENT DOCUMENTS

| 5,223,285 | A | 6/1993 | DeMichele et al. |
|---|---|---|---|
| 5,492,899 | A | 2/1996 | Masor |
| 6,485,738 | B1 | 11/2002 | Huang et al. |
| 7,090,879 | B2 | 8/2006 | Albrecht et al. |
| 7,829,126 | B2 | 11/2010 | Barrett-Reis et al. |
| 10,328,049 | B2 * | 6/2019 | Lai .................. A61K 31/355 |
| 2003/0104078 | A1 | 6/2003 | Barrett-Reis et al. |
| 2004/0202765 | A1 | 10/2004 | McMahon |
| 2005/0208179 | A1 | 9/2005 | Albrecht et al. |
| 2006/0171993 | A1 | 8/2006 | Barrett-Reis et al. |
| 2006/0205826 | A1 | 9/2006 | Romero et al. |
| 2007/0098849 | A1 | 5/2007 | Barrett-Reis et al. |
| 2008/0003330 | A1 | 1/2008 | Rueda et al. |
| 2008/0044475 | A1 | 2/2008 | Montoya et al. |
| 2011/0213039 | A1 | 9/2011 | Barrett-Reis et al. |
| 2014/0010912 | A1 | 1/2014 | Clinger et al. |
| 2015/0025133 | A1 | 1/2015 | Lai |
| 2016/0008318 | A1 | 1/2016 | Lai |

FOREIGN PATENT DOCUMENTS

| CA | 2802910 | 12/2011 |
|---|---|---|
| CN | 1397178 | 2/2003 |
| CN | 1792194 | 6/2006 |
| CN | 1802094 | 7/2006 |
| CN | 101484025 | 7/2009 |
| CN | 101856046 | 10/2010 |
| CN | 102132742 | 7/2011 |
| CN | 103402375 | 11/2013 |
| WO | 2003017945 | 3/2003 |
| WO | 2005054415 | 6/2005 |
| WO | 2007050521 | 5/2007 |
| WO | 2008103370 | 8/2008 |
| WO | 2010112429 | 10/2010 |
| WO | 2011118810 | 9/2011 |
| WO | 2012092085 | 7/2012 |
| WO | 2013101494 | 7/2013 |
| WO | 2013138157 | 9/2013 |

(Continued)

OTHER PUBLICATIONS

Silbereis et al., The Cellular and Molecular Landscapes of the Developing Human Central Nervous System, Neuron. Jan. 20, 2016; 89(2):248-68.*
MedlinePlus, Aging changes in the nervous system, National Institutes of Health, Jul. 12, 2018, printed from https://medlineplus.gov/ency/article/004023.htm, 3 pages.*
Wang, Sialic acid is an essential nutrient for brain development and cognition, Annu Rev Nutr. 2009;29:177-222, printed from https://www.ncbi.nlm.nih.gov/pubmed/19575597, Abstract only, 1 page.*
Communication pursuant to Article 94(3) EPC in EP Application No. 14716161.6 dated Dec. 12, 2016.
Communication pursuant to Article 94(3) EPC in EP Application No. 14716161.6 dated Jul. 12, 2017.

(Continued)

*Primary Examiner* — Gigi G Huang
(74) *Attorney, Agent, or Firm* — Calfee, Halter & Griswold LLP

(57) ABSTRACT

Disclosed are methods of using nutritional compositions generally, and infant formulas specifically, to improve cognitive, brain and/or central nervous system development in an individual. The nutritional compositions include a combination of RRR-alpha tocopherol acetate, non-RRR-alpha-tocopherol stereoisomers, fat, and protein. The amount of non-RRR alpha tocopherol stereoisomers in the nutritional compositions is limited.

8 Claims, No Drawings

(56) References Cited

FOREIGN PATENT DOCUMENTS

| WO | 2014105576 | 7/2014 |
|---|---|---|
| WO | 2014159967 | 10/2014 |
| WO | 2014165008 | 10/2014 |

OTHER PUBLICATIONS

Summons to Attend Oral Proceedings Pursuant to Rule 115(1) EPC in EP Application No. 14716161.6 dated Jan. 23, 2018.
Rules 161(1) and 162 Communication in EP Application No. 14716172.3 dated Oct. 21, 2015.
Communication Pursuant to Article 94(3) in EP Application No. 14716172.3 dated Dec. 15, 2016.
Office Action in IL Application No. 234553 (with English Summary of Office Action) dated Oct. 10, 2016.
Office Action in IL Application No. 240011 dated Jun. 29, 2017, blacked out portions not considered.
Office Action in IL Application No. 240750 (with English Summary) dated Sep. 11, 2017 considered English summary only.
Examination Report from Malaysian Application No. PI 2014002650 dated Sep. 15, 2017.
English Summary Office Action in Mexican Patent Application No. MX/a/2014/011056 dated Jun. 13, 2017 blacked out portions not considered.
First Examination Report for NZ 630,210 dated Jun. 12, 2015.
Further Examination Report for NZ 630,210 dated Nov. 4, 2015.
Search Report and Written Opinion in SG 11201405709S dated Jul. 9, 2015.
Written Opinion in SG Application No. 1120157217P dated Jul. 14, 2016.
Written Opinion in SG 11201405709S dated Jul. 31, 2015.
Notice of Eligibility for Grant in Singapore Patent Application No. 11201405709S dated Feb. 14, 2018.
Written Opinion in SG 11201405709S dated Feb. 7, 2017.
Written Opinion in SG 11201507212T dated Sep. 26, 2016.
Search Report in SG 11201507210X dated Jul. 29, 2016.
Written Opinion in SG 11201507210X dated Nov. 9, 2016.
Written Opinion in SG 11201507210X dated Aug. 1, 2017.
First Office Action for VN App. 1-2015-03222 dated Nov. 19, 2015.
Office Action in VN 1-2014-03398 dated Nov. 14, 2014.
National Institutes of Health, Office of Dietary Supplements, "Dietary Supplements Ingredient Database," 1 page, printed from https://dietarysupplementdatabase.usda.nih.gov/conversions.html, last updated Mar. 20, 2015, referenced on May 19, 2017.
Acuff, Robert V., et al., "Relative bioavailability of RRR-and all-rac-a-tocopheryl acetate in humans: studies using deuterated compounds 3," American Society for Clinical Nutrition, Jan. 1, 1994, pp. 397-402.
Bettler, J. et al., Serum lutein concentrations in healthy term infants fed human milk or infant formula with lutein. European Journal of Nutrition, 2010, vol. 49, pp. 45-51.
"Dhasco and Arasco Oils As Sources of Long-Chain Polyunsaturated Fatty Acids in Infant Formula," Food Standards Australia New Zealand, Jun. 2003, Sect. 2, pp. 8-12, downloaded Jun. 20, 2017.
Gualtieri, C.T. Cognitive Enhancers and Neuroprotectants. In Brain Injury and Mental Retardation (Chapter 25); Lippincott Williams & Wilkins; Philadelphia, PA (2004).
Gill, et al., Liquid chromatographic method for the determination of lutein in milk and pediatric formulas, International Dairy Journal, vol. 18, Issue 9, Sep. 2008, pp. 894-898 (cited in Office Action in U.S. Appl. No. 14/771,719 dated Sep. 9, 2016).
Holman, R.T., et al., "Deficiency of essential fatty acids and membrane fluidity during pregnancy and lactation," Proceedings of the National Academy of Sciences of the United States of America, vol. 88, No. 11, Jun. 1, 1991, pp. 4835-4839.
Jensen et al., Alpha-tocopherol stereoisomers, Vitam Horm. 2007, 76:281-308 printed from https://www.ncbi.nlm.nih.gov/pubmed/17628178, 2 pages, Abstract only.

Lebold, K. M., "Embryogenesis is dependent upon 12-lipoxygenase, 5-lipoxygenase, and a-tocopherol to modulate polyunsaturated fatty acid status and the production of oxidized fatty acids in zebrafish," Master of Science Thesis, Oregon State University, May 25, 2012.
Third Party Observations in PCT/US2013/029611 dated Jul. 3, 2014.
Rubin, et al., Effect of carotenoid supplementation on plasma carotenoids, inflammation and visual development in preterm infants, J. of Perinatology, (Jun. 2012), 32(6), pp. 418-424. DOI: 10.1038/jp.2011.87-Electronically published on Jul. 14, 2011, printed from http://www.ncbi.nlm.nih.gov/pubmed/21760585, 2 pages (abstract only).
Sheppard et al., "Analysis and Distribution of Vitamin E in Vegetable Oils and Foods," Vitamin E in Health and Disease, Jan. 1, 1993, XP055391206, pp. 9-31.
Stone et al., Infants Discriminate Between Natural and Synthetic Vitamin E, Am J Clin Nutr. Apr. 2003, 77(4), pp. 399-906, printed from https://www.ncbi.nlm.nih.gov/pubmed/12663289, Abstract only, 2 pages.
"Tocopheryl Acetate," The Dermatology Review, http://www.thedermreview.com/tocopheryl-acetate/, downloaded Jun. 14, 2017.
Yang Ying et al., "Vitamin E and vitamin E acetate solubilization in mixed micelles: physicochemical basis of boaccessibility," Sep. 1, 2013, Journal of Colloid and Interface Science, vol. 405, pp. 312-321.
Office Action in Canada Patent Application No. 2,867,438 dated Aug. 7, 2017.
International Search Report and Written Opinion for PCT/US2013/029611 dated Aug. 13, 2013.
International Preliminary Report on Patentability for PCT/US2013/029611 dated Sep. 16, 2014.
International Search Report and Written Opinion for PCT/US2014/024114 dated Jul. 31, 2014.
International Preliminary Report on Patentability for PCT/US2014/024114 dated Sep. 15, 2015.
International Search Report and Written Opinion for PCT/US2014/025541 dated Jun. 20, 2014.
International Preliminary Report on Patentability for PCT/US2014/025541 dated Sep. 15, 2015.
International Search Report and Written Opinion for PCT/US2014/026339 dated Jun. 20, 2014.
International Preliminary Report on Patentability for PCT/US2014/026339 dated Sep. 15, 2015.
Office Action in US U.S. Appl. No. 14/384,739 dated Jul. 9, 2015.
Response to Office Action in U.S. Appl. No. 14/384,739 dated Oct. 9, 2015.
Final Office Action in U.S. Appl. No. 14/384,739 dated Dec. 7, 2015.
Amendment with RCE in U.S. Appl. No. 14/384,739 dated Jun. 7, 2016.
Office Action in U.S. Appl. No. 14/384,739 dated Dec. 6, 2016.
Amendment in U.S. Appl. No. 14/384,739 dated Mar. 6, 2017.
Office Action in U.S. Appl. No. 14/384,739 dated Apr. 21, 2017.
Amendment in U.S. Appl. No. 14/384,739 dated Jul. 21, 2017.
Office Action in U.S. Appl. No. 14/384,739 dated Dec. 29, 2017.
Restriction Requirement in U.S. Appl. No. 14/774,889 dated Sep. 13, 2016.
Office Action in U.S. Appl. No. 14/774,889 dated Nov. 25, 2016.
Final Office Action in U.S. Appl. No. 14/774,889 dated May 25, 2017.
Response to Office Action in U.S. Appl. No. 14/774,889 dated Jul. 25, 2017.
Notice of Allowance in U.S. Appl. No. 14/774,889 dated Aug. 14, 2017.
Office Action in CA 2,867,438 dated Jul. 7, 2015.
Office Action in CA 2,867,438 dated Mar. 10, 2016.
Office Action in CA 2,867,438 dated Dec. 8, 2016.
Office Action in CA 2,901,457 dated Sep. 16, 2016.
Office Action in CA 2,901,457 dated Jun. 12, 2017.
Office Action in CA 2,903,703 dated Nov. 8, 2016.
First Office Action in CN Application No. 201380023797.0 dated Sep. 18, 2015.

(56) References Cited

OTHER PUBLICATIONS

Office Action in CN Application No. 201380023797.0 dated May 26, 2016.
Decision on Rejection in CN Application No. 201380023797.0 dated Jan. 26, 2017.
Notice of Reexamination in CN Application No. 201380023797.0 dated Feb. 26, 2018.
Office Action in CN Application No. 201480014237.3 dated Sep. 26, 2016.
Office Action in CN Application No. 201480014237.3 dated May 24, 2017.
Office Action in CN Application No. 201480014237.3 dated Dec. 12, 2017.
Office Action in CN Application No. 201480026211.0 dated Sep. 9, 2016.
Office Action in CN Application No. 201480026211.0 dated May 2, 2017.
Rules 161 and 162 Communication from EP Application No. 13710266.1 dated Oct. 21, 2014.
Communication pursuant to Article 94(3) EPC in EP Application No. 13710266.1 dated Aug. 28, 2015.
Communication pursuant to Article 94(3) EPC in EP Application No. 13710266.1 dated Jul. 14, 2016.
Communication pursuant to Article 94(3) EPC in EP Application No. 13710266.1 dated Jan. 4, 2017.
Communication pursuant to Article 94(3) EPC in EP Application No. 13710266.1 dated Aug. 1, 2017.
Summons to Attend Oral Proceedings Pursuant to Rule 115(1) EPC in EP Application No. 13710266.1 dated Jan. 23, 2018.
Rules 161(1) and 162 Communication in EP Application No. 14717290.2 dated Oct. 20, 2015.
Rules 161(1) and 162 Communication in EP Application No. 14716161.6 dated Nov. 5, 2015.

\* cited by examiner

METHOD OF USING A COMPOSITION FOR ENHANCING NEWBORN INFANT COGNITIVE, BRAIN AND/OR CNS DEVELOPMENT

CROSS-REFERENCE TO RELATED APPLICATIONS

This application is a divisional of U.S. application Ser. No. 14/771,719, filed Aug. 31, 2015, which is a national stage entry of International Application No. PCT/US14/25541, filed Mar. 13, 2014, which claims priority to and any benefit of U.S. Provisional Application No. 61/778,974, filed Mar. 13, 2013, the entire contents of which are incorporated by reference in their entirety.

FIELD OF THE DISCLOSURE

The present disclosure relates to nutritional compositions, such as infant formula compositions, that contain fat, protein, carbohydrates, and RRR-alpha tocopherol, wherein the composition contains a limited amount of alpha tocopherol stereoisomers which are not in the RRR configuration. More particularly, the present disclosure relates to nutritional compositions for enhancing infant brain, central nervous system, and/or cognitive development in an individual, and specifically an infant, and methods of using the same.

BACKGROUND OF THE DISCLOSURE

Infant formulas are commonly used today to provide a supplemental or sole source of nutrition early in life to both preterm and term infants. These formulas typically contain protein, carbohydrate, fat, vitamins, minerals, and other nutrients, and are commercially available as powders, ready-to-feed liquids, and liquid concentrates. Many infant formulas provide a quality alternative to human milk, as not all infants can receive human milk.

SUMMARY OF THE DISCLOSURE

The instant disclosure provides nutritional compositions, in particular infant formula compositions, that include i) from about 20 to about 50 g/L fat; ii) from about 10 to about 15 g/L protein; iii) from about 5 mg/L to about 100 mg/L RRR-alpha tocopherol; iv) less than about 8 mg/L of a non-RRR alpha tocopherol isomer; v) from about 60 mg/L to about 180 mg/L of DHA; vi) from about 120 mg/L to about 360 mg/L of ARA, wherein the DHA to RRR alpha tocopherol ratio is from about 7.5:1 to about 20:1 and the ratio of ARA to RRR alpha tocopherol is from about 15:1 to about 40:1; and vi) at least about 130 mg/L of ascorbic acid.

In another aspect, the instant disclosure provides methods of enhancing central nervous system maturation in an infant by administering a composition as disclosed herein.

Accordingly, the nutritional compositions and methods of the present disclosure offer an alternative therapeutic or nutritional intervention option that may contribute to the enhancement of brain development, enhanced central nervous system development, and/or improvement of cognitive performance in individuals, and, particularly, in infants, toddlers, or children.

DETAILED DESCRIPTION OF THE DISCLOSURE

It is important that early in life infants receive sufficient nutrition to provide for adequate maturation both physically and mentally, and specifically in the brain and central nervous system. Insufficient nutrition can result in numerous life-long health problems. In particular, brain and central nervous system maturation are key developmental areas for infants.

Applicants have discovered that levels of brain RRR alpha tocopherol correlate with brain cholesterol. Cholesterol is a major component of myelin, and neuron myelination is a critical step of CNS development. The white matter of the brain contains a higher lipid and cholesterol content as compared to the gray matter due to the increased amount of myelin in the white matter. Neuron myelination increases signal transmission speed drastically, which, in turn, allows the brain to perform complex processes. Further, the level of brain glutamate is believed to correlate with RRR alpha tocopherol. Glutamate has been reported to stimulate neuron elongation and branching. The establishment of gap junctions among neurons facilitates fast communication among neurons to allow the brain to perform complicated tasks. Thus, establishing gap junctions among neurons is a critical step of CNS maturation.

Applicants have found that in the brains of infants, breast fed infants had a higher level of myelination as indicated by the higher lipid and cholesterol content. It has been reported that there is a protein called supernatant protein factor that binds alpha tocopherol. This complex stimulates cholesterol synthesis, thereby increasing myelination in the brain. The brains of infants fed breast milk accrete RRR alpha tocopherol at a faster rate than formula fed infants. It is reported that the RRR isomer of alpha tocopherol in cow's milk accounts for more than 80% of the total alpha tocopherol isomers in the milk even when the cow diet is supplemented with a high dose of synthetic all-rac-alpha tocopherol (also referred to as tocopherol acetate, which is an equimolar mixture of eight isomers, only one of which is RRR-alpha tocopherol). Most infant formula is fortified with all-rac-alpha tocopherol. Only one eighth of the all-rac-alpha tocopherol is of the RRR alpha tocopherol isomer. Applicants have found that while both formula and breast milk fed infants have about the same level of alpha tocopherol, the brains of formula fed infants contain more non-RRR alpha tocopherol. (See Example 1.)

Without intending to be limited by theory, it is believed that the non-RRR isomers compete with RRR alpha tocopherol to compromise the beneficial effect on CNS maturation. It is Applicants belief that by limiting the amount of non RRR-alpha tocopherol isomers, the efficacy and the accretion rate of RRR-alpha tocopherol can be enhanced thereby benefiting CNS development.

The instant disclosure provides compositions and methods believed to result in improved formulations that enhance cognitive, CNS, and/or brain development, due to limiting the amount of non-RRR alpha tocopherol isomers that may interfere with the formation of the required complex described above. Use of the disclosed compositions as described herein may provide an effective formulation for improvement of cognitive, brain, and/or CNS development in infants.

A particular formulation of the composition includes i) from about 20 to about 50 g/L fat; ii) from about 10 to about 15 g/L protein; iii) from about 5 mg/L to about 100 mg/L RRR-alpha tocopherol; iv) less than about 8 mg/L of a non-RRR alpha tocopherol isomer; v) from about 60 mg/L to about 180 mg/L of DHA; vi) from about 120 mg/L to about 360 mg/L of ARA, wherein the DHA to RRR alpha tocopherol ratio is from about 7.5:1 to about 20:1 and the ratio of ARA to RRR alpha tocopherol is from about 15:1 to about 40:1; and vi) at least about 130 mg/L of ascorbic acid.

Also provided are methods of enhancing central nervous system maturation in an infant by administering a composition disclosed herein. A particular form of the method includes administering a composition which includes about 20 to about 40 grams/L of fat, about 10 to about 15 grams/L of protein, at least 5 mg/L of RRR-alpha tocopherol, and no more than 8 mg/L of a non-RRR alpha tocopherol isomer.

These and other elements or features of the various embodiments are described in detail hereafter.

The terms "aseptic" and "aseptic sterilized" are used interchangeably herein, and unless otherwise specified, refer to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The term "cognitive performance" as used herein, unless otherwise specified, refers to the learning, thinking, and memory functions (i.e., memory acquisition, memory retention and memory recall) of the brain. Accordingly, the term "improving cognitive performance" as used herein, unless otherwise specified, refers to improving the learning, thinking, and/or memory (memory acquisition, memory retention and memory recall) functions of an infant.

The terms "fat," "lipid" and "oil" as used herein, unless otherwise specified, are used interchangeably to refer to lipid materials derived or processed from plants or animals. These terms also include synthetic lipid materials so long as such synthetic materials are suitable for oral administration to humans.

The term "infant" as used herein, refers generally to individuals up to age 36 months of age, actual or corrected. The term "preterm infant," as used herein, refers to an infant born prior to 36 weeks of gestation. The term "term infant," as used herein, refers to an infant born at or after 36 weeks of gestation. The term "newborn infant," as used herein, unless otherwise specified, refers to infants less than about 3 months of age, including infants from zero to about 2 weeks of age. A newborn infant may be a term or preterm infant.

The term "non-RRR alpha tocopherol isomers" as used herein, means alpha tocopherol stereoisomers which are not in the RRR configuration. In other words, the term encompasses all or any of the SSS, SSR, SRR, SRS, RSS, RRS, RRR, and RSR stereoisomers of alpha tocopherol. Unless stated otherwise, when amounts of non-RRR alpha tocopherol isomers are referred to herein, the numbers refer to the total amount of all non-RRR alpha tocopherol isomers.

The terms "nutritional composition," "nutritional product," and "nutritional formula" as used herein, unless otherwise specified, are used interchangeably to refer to nutritional liquids and nutritional powders that comprise at least one of protein, fat, and carbohydrate and are suitable for oral administration to a human. The nutritional composition may further comprise vitamins, minerals, and other ingredients and represent a sole, primary, or supplemental source of nutrition. Nutritional compositions include infant formulas but do not include breast milk.

The term "nutritional liquid," as used herein, unless otherwise specified, refers to nutritional products in ready-to-drink liquid form, concentrated form, and nutritional liquids made by reconstituting the nutritional powders described herein prior to use.

The term "nutritional powder," as used herein, unless otherwise specified, refers to nutritional products in flowable or scoopable form that can be reconstituted with water or another aqueous liquid prior to consumption and includes both spray dried and dry mixed/dryblended powders.

The terms "retort" and "retort sterilized" are used interchangeably herein, and unless otherwise specified, refer to the common practice of filling a container, most typically a metal can or other similar package, with a nutritional liquid, such as a liquid infant formula, and then subjecting the liquid-filled package to the necessary heat sterilization step, to form a retort sterilized nutritional liquid product.

The term "ready-to-feed" as used herein, unless otherwise specified, refers to infant formulas in liquid form suitable for administration to an infant, including human reconstituted powders, which may be reconstituted with human milk or formula in addition to water, diluted concentrates, and manufactured liquids.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified. All numerical ranges as used herein, whether or not expressly preceded by the term "about," are intended and understood to be preceded by that term, unless otherwise specified. All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

Any reference to a singular characteristic or limitation of the present disclosure shall include the corresponding plural characteristic or limitation, and vice versa, unless otherwise specified or clearly implied to the contrary by the context in which the reference is made.

The various embodiments of the nutritional compositions of the present disclosure may also be substantially free of any ingredient or feature described herein, provided that the remaining formula still contains all of the required ingredients or features as described herein. In this context, and unless otherwise specified, the term "substantially free" means that the selected composition contains less than a functional amount of the optional ingredient, typically less than 1%, including less than 0.5%, including less than 0.1%, and also including zero percent, by weight of such optional or selected essential ingredient.

The nutritional compositions may comprise, consist of, or consist essentially of the elements of the products as described herein, as well as any additional or optional element described herein or otherwise useful in nutritional product applications.

All documents (patents, patent applications and other publications) cited in this application are incorporated herein by reference in their entirety.

Product Form

The nutritional compositions of the present disclosure include a combination of RRR-alpha-tocopherol, fat and protein, wherein the presence of non-RRR isomers are limited, and, optionally, one or more components as described herein, and may be formulated and administered in any known or otherwise suitable oral product form. Any solid, semi-solid, liquid, semiliquid, or powder form, including combinations or variations thereof, are suitable for use herein, provided that such forms allow for safe and effective oral delivery to the individual of the essential ingredients as also defined herein.

Specific non-limiting examples of product forms suitable for use with products and methods disclosed herein include, for example, liquid and powder preterm infant formulas, liquid and powder term infant formulas, liquid and powder toddler formulas, and liquid and powder elemental and semi-elemental formulas.

The nutritional compositions of the present disclosure are preferably formulated as dietary product forms, which are defined herein as those embodiments comprising the ingredients of the present disclosure in a product form that also contains at least one of fat, protein, and carbohydrate. The compositions may be formulated with sufficient kinds and amounts of nutrients to provide a sole, primary, or supplemental source of nutrition, or to provide a specialized nutritional product such as for use in infants afflicted with specific diseases or conditions or with a targeted nutritional benefit.

The nutritional compositions of the present disclosure may also be formulated in product forms such as capsules, tablets, pills, caplets, gels, liquids (e.g., suspensions, solutions, emulsions, clear solutions), powders or other particulates, and so forth. These product forms generally contain only the ingredients as described herein, optionally in combination with other actives, processing aids or other dosage form excipients.

The nutritional compositions of the present disclosure, when formulated as a dietary product form, may potentially provide either a sole source or a supplemental source of nutrition to an individual. In this context, a sole source of nutrition is one that can be administered once or multiple times each day to potentially provide an individual with all or substantially all their fat, protein, carbohydrate, mineral, and vitamin needs per day or during the intended period of administration. A supplemental source of nutrition is defined herein as a dietary source that does not provide an individual with a potentially sole source of nutrition.

The nutritional compositions of the present disclosure may be formulated as milk protein-based liquids, soy protein-based liquids, low-pH liquids, clear liquids, reconstitutable powders, nutritional bites (e.g., plurality of smaller dietary product dosage forms in a single package), or nutritional bars (snack or meal replacement).

Nutritional Liquids

Nutritional liquids may include both concentrated and ready-to-feed nutritional liquids. These nutritional liquids are most typically formulated as suspensions, emulsions or clear or substantially clear liquids.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional liquids may be and typically are shelf stable. The nutritional liquids may contain up to 95% by weight of water, including from about 50% to about 95%, also including from about 60% to about 90%, and also including from about 70% to about 87%, of water by weight of the nutritional liquid. The nutritional liquids may have a variety of product densities, but most typically have a density greater than 1.03 g/mL, including greater than 1.04 g/mL, including greater than 1.055 g/mL, including from about 1.06 g/mL to about 1.12 g/mL, and also including from about 1.085 g/mL to about 1.10 g/mL.

The nutritional liquid may have a pH ranging from about 3.5 to about 8, but are most advantageously in a range of from about 4.5 to about 7.5, including from about 5.5 to about 7.3, including from about 6.2 to about 7.2.

Although the serving size for the nutritional liquid can vary depending upon a number of variables, a typical serving size is generally at least 2 mL, or even at least 5 mL, or even at least 10 mL, or even at least 25 mL, including ranges from 2 mL to about 300 mL, including from about 100 mL to about 300 mL, from about 4 mL to about 250 mL, from about 150 mL to about 250 mL, from about 10 mL to about 240 mL, and from about 190 mL to about 240 mL.

Nutritional Powders

The nutritional powders may be in the form of flowable or substantially flowable particulate compositions, or at least particulate compositions. Particularly suitable nutritional powder forms include spray dried, agglomerated or dry-blended powder compositions, or combinations thereof, or powders prepared by other suitable methods. The compositions may be easily be scooped and measured with a spoon or similar other device, wherein the compositions can easily be reconstituted with a suitable aqueous liquid, typically water, to form a nutritional liquid, such as an infant formula, for immediate oral or enteral use. In this context, "immediate" use generally means within about 48 hours, most typically within about 24 hours, preferably right after or within 20 minutes of reconstitution.

RRR-Alpha Tocopherol

The nutritional compositions of the present disclosure include RRR-alpha tocopherol, which means that the nutritional compositions are either formulated with the addition of RRR-alpha tocopherol or are otherwise prepared so as to contain RRR-alpha tocopherol. As used herein, the term "RRR-alpha tocopherol" refers to both exogenous sources and inherent sources of free RRR-alpha tocopherol and RRR-alpha tocopherol esters such as RRR alpha tocopherol acetate that are present in a nutritional composition, including an infant formula. Inherent sources include RRR-alpha tocopherol that is inherently present in components that are present in a nutritional composition and include, for example, various oils and fats. Exogenous sources of RRR-alpha tocopherol include RRR-alpha tocopherol acetate that is added to the nutritional composition not as part of another component. Any source of RRR-alpha tocopherol is suitable for use herein provided that the finished product contains RRR-alpha tocopherol.

Tocopherols, generically referred to as vitamin E, are available in four forms, alpha, beta, gamma, and delta, which differ in the number and position of the methyl groups on the chroman ring (see Table 1). Further, tocopherols can exist in a number of stereoisomeric forms depending on the chirality of the phytyl tail. Of the alpha tocopherols, RRR-alpha tocopherol (also referred to as "natural vitamin E") has the greatest biological activity and is reported to be the dominant form of the alpha tocopherol in the brain. RRR-alpha tocopherol is a single stereoisomer whereas synthetic vitamin E (all-rac-alpha tocopherol or tocopherol acetate) is an equimolar mixture of eight isomers, only one of which is RRR-alpha tocopherol. The fact that the dominant form of alpha tocopherol in the brain is RRR alpha tocopherol (based on animal studies) strongly suggests that the other seven chiral isomers must be absorbed at a lower rate by the brain or oxidized at a faster rate. Cholesterol is a major component of myelin. As such, it is likely that stimulated cholesterol synthesis will stimulate newborn infant neuron myelination.

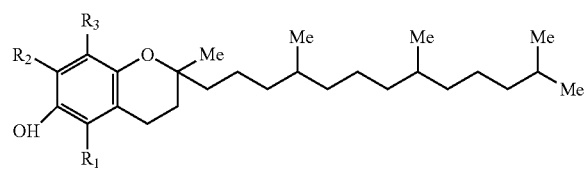

TABLE 1

| Compound | R1 | R2 | R3 |
|---|---|---|---|
| alpha-tocopherol | Me | Me | Me |
| beta-tocopherol | Me | H | Me |
| gamma-tocopherol | H | Me | Me |
| delta-tocopherol | H | H | Me |

The disclosed compositions include RRR-alpha tocopherol in an amount sufficient to improve brain or CNS development. In some aspects, the nutritional compositions includes concentrations of RRR-alpha tocopherol of at least about 5 mg/L, including at least about 7 mg/L, including at least about 8 mg/L, including at least about 9 mg/L, including at least about 10 mg/L, including at least about 15 mg/L, including at least about 18 mg/L, including at least about 20 mg/L, also including from at least about 5 mg/L to about 100 mg/L, including from at least about 7 mg/L to about 50 mg/L, and including from about 20 mg/L to about 40 mg/L of the composition. The total amounts of RRR-alpha tocopherol may include both exogenous and inherent amounts of RRR-alpha tocopherol, as noted above.

The nutritional compositions of the present disclosure may include LC-PUFAs in addition to the other components listed above. LC-PUFAs may be included in the nutritional compositions to provide nutritional support and benefits, as well as to support brain development in individuals, and specifically in infants. In some embodiments, the nutritional compositions may include a combination of LC-PUFAs with the RRR-alpha tocopherol. LC-PUFAs may be provided in the disclosed compositions as free fatty acids, in triglyceride form, in diglyceride form, in monoglyceride form, in phospholipid form, or as a mixture of one or more of the above, preferably in triglyceride form. Particularly suitable for use in the nutritional compositions in addition to the RRR-alpha tocopherol, are combinations of arachidonic acid (ARA) and docosahexaenoic acid (DHA). ARA is an n-6 LC-PUFA that is present in the phospholipids, especially phosphatidylethanolamine, phosphatidylcholine, and phosphatidylinositides, of membranes of the body's cells, and is abundant in the brain, muscles, and liver, and DHA is an n-3 LC-PUFA that is abundant in the brain and retina, accounting for 40% of the LC-PUFAs in the brain and 60% of the LC-PUFAs in the retina.

In one specific embodiment, the nutritional compositions include DHA in a concentration of at least 60 mg/L, including at least 70 mg/L, including at least 80 mg/L, including at least 90 mg/L, including at least 100 mg/L, including at least 150 mg/L, including at least 200 mg/L and also including from 60 mg/L to about 1000 mg/L, including from about 60 mg/L to about 180 mg/L, and include ARA in a concentration of at least 110 mg/L, including at least 120 mg/L, including at least 130 mg/L, including at least 140 mg/L, including at least 150 mg/L, including at least 200 mg/L, and also including from 110 mg/L to about 1000 mg/L, including from about 110 mg/L to about 500 mg/L, including from about 120 mg/L to about 360 mg/L.

DHA and ARA are very prone to oxidation and they can be oxidized by the mucosa xanthine oxidase. The resulting lipid peroxide may oxidize RRR alpha tocopherol before RRR alpha tocopherol can reach circulation. Thus, where ARA and DHA are added to the compositions, RRR alpha tocopherol may be preserved by optimization of the ratio between ARA/RRR alpha tocopherol and DHA/RRR alpha tocopherol. In some embodiments, the nutritional compositions includes combinations of RRR-alpha tocopherol, DHA and ARA such that the weight ratio of DHA to RRR-alpha tocopherol ranges from about 7.5:1 to about 20:1, or from about 8:1 to about 15:1, and the weight ratio of ARA to RRR-alpha tocopherol ranges from about 15:1 to about 40:1, including from about 16:1 to about 32:1.

Vitamin C is an anti-oxidant that may also be added to the disclosed compositions. In some embodiments, the nutritional compositions of the present disclosure include vitamin C to quench the free radical from DHA and ARA oxidization to provide RRR-alpha tocopherol oxidative protection. Vitamin C, also referred to as L-ascorbic acid or L-ascorbate, is available from many fruit and vegetable sources. Any source of vitamin C that is suitable for use in an oral nutritional product and is compatible with the essential elements and features of such products may be used with the nutritional compositions of the present disclosure.

Vitamin C may chelate free ferrous iron, which has been found to lower serum vitamin E levels in formula fed pre-term infants, thereby preventing iron from acting as a pro-oxidant. Including vitamin C in the compositions of the present disclosure may reduce the oxidative degradation of RRR-alpha tocopherol.

Accordingly, vitamin C may also or alternatively be included in the infant formulas of the present disclosure to reduce the oxidative degradation of RRR-alpha tocopherol. In this aspect, the nutritional compositions of the present disclosure include vitamin C in a concentration of at least about 130 mg/L, including at least 150 mg/L, including at least 175 mg/L, including at least 200 mg/L, including at least 225 mg/L, including at least 250 mg/L, including at least 300 mg/L and also including from 130 mg/L to about 1000 mg/L, including from about 200 mg/L to about 500 mg/L.

Non-RRR Alpha Tocopherol Isomers

The nutritional compositions disclosed herein, in some aspects, are substantially free of non-RRR alpha tocopherol isomers. In other aspects, the composition includes less than about 9 mg/L, or less than about 8 mg/L, or less than about 7 mg/L, or less than about 6 mg/L, or less than about 5 mg/L, or less than about 4 mg/L, or less than about 3 mg/L, or less than about 2 mg/L, or less than about 1 mg/L, or less than about 0.5 mg/L non-RRR alpha tocopherol isomers (in total). In other aspects, the amount of non-RRR-alpha tocopherol isomers are limited to an amount that allows RRR-alpha tocopherol to effectively enhance brain, CNS, and/or cognitive development in an individual, particularly an infant. In one aspect, the compositions are substantially free of non-RRR alpha tocopherol isomers.

In certain embodiments, the nutritional compositions disclosed herein, contain relatively more RRR-alpha tocopherol than a racemic mixture of alpha tocopherol, and, as a result, contain less of the non-RRR alpha tocopherol isomers. In certain such embodiments, the ratio of RRR-alpha tocopherol to non-alpha tocopherols is at least about 1:7, including 1:7-99:1, which translates to about at least about 14% RRR alpha tocopherol. In additional such embodiments, the ratio of RRR-alpha tocopherol to non-RRR alpha tocopherol is 1:5 to 99:1, including 1:4 to 99:1, 1:3 to 99:1, 1:2 to 99:1, 1:1 to 99:1, 2:1 to 99:1, 3:1 to 99:1, and 4:1 to 99:1.

Protein

The nutritional compositions include one or more proteins in addition to the RRR-alpha tocopherol described above. In some aspects, the protein of the nutritional compositions may comprise from about 0.1% to about 100% of the total calories, including from about 5% to about 40%, including from about 5% to about 20%, including from about 15% to about 25%. Proteins suitable for use in the nutritional compositions may include hydrolyzed, partially hydrolyzed or non-hydrolyzed proteins or protein sources, and can be derived from any known or otherwise suitable source such as milk (e.g., casein, whey), animal (e.g., meat, fish, egg albumen), cereal (e.g., rice, corn), vegetable (e.g., soy, pea, potato), or combinations thereof. The proteins for use herein may also include, or be entirely or partially replaced by, free amino acids known for use in nutritional products, non-limiting examples of which include L-tryptophan, L-glutamine, L-tyrosine, L-methionine, L-cysteine, taurine, L-arginine, L-carnitine, and combinations thereof.

For solid embodiments of the nutritional compositions of the present disclosure, the solid embodiments generally comprise protein in quantities ranging up to about 30%, including from about 5% to about 25%, and also including from about 10% to about 20%, and also including from about 12% to about 16%, by weight of the solid nutritional composition.

For liquid embodiments of the nutritional compositions of the present disclosure, the liquid embodiments may comprise protein in quantities ranging up to 30%, including from about 1% to about 20%, and also including from about 1% to about 10%, and also including from about 5% to about 8%, by weight of the liquid nutritional composition. Alternatively, the amount of protein can be represented by the amount of protein per liter of liquid nutritional composition.

The nutritional compositions of the present disclosure may optionally comprise a soy protein component, sources of which include, but are not limited to, soy flakes, soy protein isolates, soy protein concentrate, hydrolyzed soy protein, soy flour, soy protein fiber, or any other protein or protein source derived from soy. Commercial sources of soy protein are well known in the nutrition art, some non-limiting examples of which include soy protein isolates distributed by The Solae Company (St. Louis, Mo.) under the trade designation "Soy Protein Isolate EXP-H0118," "EXP-E-0101, and "Supro Plus 675." The optional soy protein component may represent from zero to about 100%, including from about 10% to about 100%, and including from about 15% to 100%, and also including from about 75% to about 95%, and also including from about 80% to about 90% of the total protein calories in the composition.

Fat

The nutritional compositions disclosed herein include fat or a source of fat. Fats suitable for use in the nutritional compositions include coconut oil, fractionated coconut oil, soy oil, corn oil, olive oil, safflower oil, high oleic safflower oil, high GLA-safflower oil, MCT oil (medium chain triglycerides), sunflower oil, high oleic sunflower oil, palm and palm kernel oils, palm olein, canola oil, marine oils, flaxseed oil, borage oil, cottonseed oils, evening primrose oil, blackcurrant seed oil, transgenic oil sources, fungal oils, marine oils (e.g., tuna, sardine), and so forth.

The nutritional compositions of the present disclosure may optionally comprise a flaxseed component, non-limiting examples of which include ground flaxseed and flaxseed oil. Ground flaxseed is generally preferred. Non-limiting examples of flaxseed include red flaxseed, golden flaxseed, and combinations thereof. Golden flaxseed is generally preferred. Commercial sources of flaxseed are well known in the nutrition and formulation arts, some non-limiting examples of which include flaxseed and flax products available from the Flax Council of Canada, the Flax Consortium of Canada, and Heintzman Farms (North Dakota) (Dakota Flax Gold brand).

The nutritional compositions include a fat. In some embodiments where the nutritional composition is a solid, the nutritional composition includes fat in quantities ranging up to about 35%, including from about 5% to about 30%, and also including from about 10% to about 25%, and also including from about 15% to about 20%, by weight of the solid nutritional composition.

For liquid embodiments of the nutritional compositions of the present disclosure, the liquid embodiments include fat in quantities ranging up to about 30%, including from about 1% to about 20%, and also including from about 1% to about 10%, and also including from about 5% to about 9%, by weight of the liquid nutritional composition.

Optional Ingredients

Carbohydrates

The nutritional compositions may further comprise one or more carbohydrates. Carbohydrates suitable for use in the nutritional compositions may be simple, complex, or variations or combinations thereof, all of which are optionally in addition to the components described herein. Non-limiting examples of suitable carbohydrates include hydrolyzed or modified starch or cornstarch, maltodextrin, isomaltulose, sucromalt, glucose polymers, sucrose, corn syrup, corn syrup solids, rice-derived carbohydrate, glucose, fructose, lactose, high fructose corn syrup, honey, sugar alcohols (e.g., maltitol, erythritol, sorbitol), and combinations thereof.

Carbohydrates suitable for use herein may include soluble dietary fiber, non-limiting examples of which include gum Arabic, fructooligosaccharide (FOS), sodium carboxymethyl cellulose, guar gum, citrus pectin, low and high methoxy pectin, oat and barley glucans, carrageenan, *psyllium* and combinations thereof. Insoluble dietary fiber may also be suitable as a carbohydrate source herein, non-limiting examples of which include oat hull fiber, pea hull fiber, soy hull fiber, soy cotyledon fiber, sugar beet fiber, cellulose, corn bran, and combinations thereof.

The nutritional compositions may therefore, and desirably, further comprise a carbohydrate, wherein for solid embodiments of the nutritional compositions of the present disclosure, the solid embodiments generally comprise carbohydrates in quantities ranging up to about 75%, including from about 20% to about 70%, and also including from about 50% to about 70%, and also including from about 55% to about 65%, and also including from about 58% to about 62%, by weight of the solid nutritional composition.

For liquid embodiments of the nutritional compositions of the present disclosure, the liquid embodiments generally comprise carbohydrate in quantities ranging up to about 30%, including from about 5% to about 25%, and also including from about 10% to about 20%, and also including from about 15% to about 18%, by weight of the liquid nutritional composition.

The concentration or amount of optional carbohydrate in the nutritional compositions can vary considerably depending upon the particular product form (e.g., bars or other solid dosage forms, milk or soy-based liquids or other clear beverages, reconstitutable powders, etc.) and the various other formulations and targeted dietary needs. Macronutrients may be formulated within any of the embodied ranges described in the following tables.

TABLE 2

| Nutrient | Embodiment A (% Total Cal.) | Embodiment B (% Total Cal.) | Embodiment C (% Total Cal.) |
|---|---|---|---|
| Carbohydrate | 0-98 | 2-96 | 10-75 |
| Protein | 0-98 | 2-96 | 5-70 |
| Fat | 0-98 | 2-96 | 20-85 |

| | Embodiment D (% Total Cal.) | Embodiment E (% Total Cal.) | Embodiment F (% Total Cal.) |
|---|---|---|---|
| Carbohydrate | 30-50 | 25-50 | 25-50 |
| Protein | 15-35 | 10-30 | 5-30 |
| Fat | 35-55 | 1-20 | 2-20 |

Each numerical value preceded by the term "about"

Carotenoids

In some embodiments, the nutritional compositions additionally include carotenoids to provide additional oxidative protection, as well as to further enhance brain development of the infant. In exemplary embodiments, the nutritional compositions include lutein, beta-carotene, zeaxanthin, lycopene, and combinations thereof. In one specific embodiment, the nutritional composition includes one or more of lutein and zeaxanthin. In one aspect, the compositions contain trans-lutein. As used herein, "trans lutein" refers to a compound having the following structure:

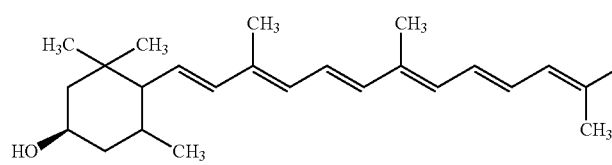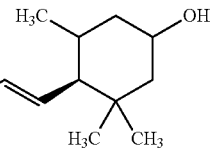

It is generally desirable that the nutritional composition comprises at least one of lutein, lycopene, zeaxanthin, beta-carotene to provide a total amount of carotenoid of from about 0.001 jig/mL to about 5 jig/mL. More particularly, the nutritional compositions may comprise lutein in an amount of from 0.001 jig/mL to 5 jig/mL, including from 0.001 jig/mL to 0.0190 jig/mL, including from 0.001 jig/mL to 0.0140 jig/L, and also including from 0.044 jig/mL to 5 jig/mL of lutein. In one aspect, the nutritional compositions include trans-lutein in an amount of from about 20 to about 50, including from about 150 to about 200. In some aspects, the carotenoid in the nutritional composition contains trans-lutein in combination with other lutein forms. In a particular aspect, the carotenoid in the nutritional composition is lutein in all-trans form.

The nutritional compositions may comprise from about 0.001 jig/mL to 5 jig/mL, from 0.001 jig/mL to 0.0130 jig/mL, including from 0.001 jig/mL to 0.0075 jig/mL of lycopene, and also including from 0.0185 jig/L to 5 jig/L of lycopene. The nutritional compositions may comprise from 1 jig/mL to 5 jig/mL, including from 0.001 jig/mL to 0.025 jig/L of beta-carotene, including from 0.001 jig/L to 0.011 jig/mL of beta-carotene, and also including from 0.034 jig/mL to 5 jig/mL of beta-carotene. It should be understood that any combination of these amounts of beta-carotene, lutein, zeaxanthin, and lycopene can be included in the nutritional compositions of the present disclosure. Other carotenoids may optionally be included in the infant formulas as described herein. Any one or all of the carotenoids included in the infant formulas described herein may be from a natural source, or artificially synthesized.

Each of the carotenoids in the selected combinations can be obtained from any known or otherwise suitable material source for use in infant formulas, and each can be provided individually, or all together, or in any combination and from any number of sources, including sources such as multivitamin premixes containing other vitamins or minerals in combination with one or more of the carotenoids as described herein. Non-limiting examples of some suitable sources of lutein, lycopene, beta-carotene, or combinations thereof include LycoVit® lycopene (available from BASF, Mount Olive, N.J.), Lyc-O-Mato® tomato extract in oil, powder, or bead form (available from LycoRed Corp., Orange, N.J.), beta-carotene, lutein, or lycopene (available from DSM Nutritional Products, Parsippany, N.J.), Flora-GLO® lutein (available from Kemin Health, Des Moines, Iowa), Xangold® Natural Lutein Esters (available from Cognis, Cincinnati, Ohio), and Lucarotin® beta-carotene (available from BASF, Mount Olive, N.J.). Trans lutein may be obtained from any suitable material source for use in the present nutritional supplements.

Other Optional Ingredients

The nutritional compositions as described herein may further comprise other optional ingredients that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, anti-oxidants, emulsifying agents, buffers, human milk oligosaccharides and other prebiotics, probiotics, nucleotides, carotenoids, pharmaceutical actives, additional nutrients as described herein, colorants, flavors, thickening agents and stabilizers, emulsifying agents, lubricants, and so forth, and combinations thereof.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional product varies depending upon the product form, the other selected ingredients, the desired flow properties, and so forth, but most typically range from about 0.1% to about 4%, including from about 0.5% to about 2%, by weight of the composition.

A stabilizer may also be included in the nutritional compositions. Any stabilizer that is known or otherwise suitable for use in a nutritional product is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

The nutritional composition may further comprise any of a variety of vitamins, non-limiting examples of which include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and combinations thereof.

The nutritional composition may also further comprise any of a variety of minerals known or otherwise suitable for use in nutritional compositions, non-limiting examples of which include phosphorus, magnesium, calcium as described hereinbefore, zinc, manganese, copper, iodine, sodium, potassium, chloride, selenium, and combinations thereof.

Methods of Manufacture

The nutritional compositions may be prepared by any known or otherwise effective manufacturing technique for preparing the selected product form. Many such techniques are known for any given product form such as nutritional liquids and nutritional powders and can easily be applied by one of ordinary skill in the nutrition and formulation arts to the nutritional products described herein.

Liquid, milk or soy-based nutritional liquids, for example, may be prepared by first forming an oil and protein blend containing all formulation oils, any emulsifier, stabilizers and fat-soluble vitamins. Additional slurries (typically a carbohydrate and protein slurries) are prepared separately by mixing the carbohydrate and minerals together and the protein in water. The slurries are then mixed together with the oil blend. The resulting mixture is heat processed, homogenized, and standardized with any water-soluble vitamins, flavored and dilution water. The standardized liquid product is placed in appropriate containers then terminally sterilized or aseptically filled. The homogenized and standardized blend can also be dried to produce a powder.

The nutritional compositions of the present disclosure may also be manufactured by other known or otherwise suitable techniques not specifically described herein without departing from the spirit and scope of the present disclosure. The present embodiments are, therefore, to be considered in all respects as illustrative and not restrictive and that all changes and equivalents also come within the description of the present disclosure.

Methods of Use

The methods of the present disclosure include the oral administration of the nutritional compositions, and, in some aspects, infant formulas, that include RRR-alpha tocopherol, fat, and protein to enhance brain development. The methods include administration of a nutritional composition including about 20 to about 40 grams/L of fat, about 10 to about 15 grams/L of protein, at least 5 mg/L of RRR-alpha tocopherol, and no more than 8 mg/L of a non-RRR alpha tocopherol isomer. In some aspects, the methods include the administration of nutritional compositions having one or more of additional properties (e.g., ingredients and/or concentrations of ingredients) of nutritional compositions disclosed above. Thus, in one aspect, the method involves administering a nutritional composition that includes less than 5 mg/L of non-RRR alpha tocopherol isomers. In another aspect, the administered nutritional composition includes one or more of a carbohydrate, a polyunsaturated fatty acid, a carotenoid, ascorbic acid, trans-lutein, and combinations thereof. In a particular aspect, the administered nutritional composition includes a carotenoid. In another aspect, the administered nutritional composition includes a trans-lutein, and, more particularly, all trans-lutein. In another particular aspect, the administered nutritional composition includes ascorbic acid. In a specific aspect, the administered nutritional composition contains a combination of properties of the above-disclosed nutritional compositions. In this aspect, the administered nutritional composition additionally contains at least about 130 mg/L of ascorbic acid, from about 60 mg/L to about 180 mg/L of DHA, and from about 120 mg/L to about 360 mg/L of ARA. In this aspect the RRR alpha tocopherol, ARA, and DHA are present in concentrations such that the DHA to RRR alpha tocopherol ratio is from about 7.5:1 to about 20:1, and the ARA to RRR alpha tocopherol ratio is from about 15:1 to about 40:1.

In addition to enhancing brain development, the nutritional compositions can be administered to improve cognitive performance, including cognitive development, in an individual, including in an infant. Particularly, the disclosed combination of RRR-alpha tocopherol, fat, and protein, wherein the presence of non-RRR isomers are limited, including where the administered nutritional composition is substantially free of a non-RRR alpha tocopherol isomer, may improve general cognition by enhancing memory acquisition, memory retention and memory recall that contributes to the cognitive functions of learning, thinking, and memory.

The nutritional compositions as described herein can be administered to individuals including infants generally, or may, in some embodiments, be administered to a specific subclass of infants that are "in need thereof," that is, to specific infants that would specifically benefit by administration of the infant formula. For example, a specific infant may be "in need of" the infant formulas as described herein if they are susceptible to (i.e., genetically predisposed, have a family history of, and/or having symptoms of the disease or condition) neurodegenerative diseases or other diseases and conditions that can impair/reduce cognition generally or specific aspects of cognition.

The individual desirably consumes at least one serving of the nutritional composition daily, and in some embodiments, may consume two, three, or even more servings per day. Each serving is desirably administered as a single, undivided dose, although the serving may also be divided into two or more partial or divided servings to be taken at two or more times during the day. The methods of the present disclosure include continuous day after day administration, as well as periodic or limited administration, although continuous day after day administration is generally desirable. The methods of the present disclosure are preferably applied on a daily basis, wherein the daily administration is maintained continuously for at least 3 days, including at least 5 days, including at least 1 month, including at least 6 weeks, including at least 8 weeks, including at least 2 months, including at least 6 months, desirably for at least about 18-24 months, desirably as a long term, continuous, daily, dietary source or supplement.

EXAMPLES

The following examples illustrate specific data and/or illustrate specific embodiments of the nutritional products of the present disclosure. The examples are given solely for the purpose of illustration and are not to be construed as limitations of the present disclosure, as many variations thereof are possible without departing from the spirit and scope of the disclosure.

Example 1

Infant brain samples were analyzed for alpha tocopherol stereo isomers using the method published by Soren et al. (2006 British J. of Nutrition 95:477). Because humans do not synthesize beta-cryptoxanthin, and infant formulas are not fortified with beta-cryptoxanthin, it is assumed that the brain samples containing beta-cryptoxanthin are from infants that were breast fed. The table below shows brain cholesterol, lipid, total alpha tocopherol and non-RRR alpha tocopherol contents of the presumed formula and breast milk fed infants.

TABLE 3

|  | Total alpha tocopherol (μg/g) | Non RRR alpha tocopherol (μg/g) | Brain Lipid (%) | Brain Cholesterol (μg/g) |
| --- | --- | --- | --- | --- |
| Breast Milk fed Infant | 10.83 | 2.76 | 3.92 | 7640 |
| Formula fed Infant | 10.78 | 3.82 | 3.56 | 6200 |

The exemplified products are nutritional products prepared in accordance with manufacturing methods well known in the nutrition industry for preparing nutritional liquids (e.g., emulsions) and powders.

Examples 2-6

Examples 2-6 illustrate ready-to-feed nutritional emulsions of the present disclosure, the ingredients of which are listed in the table below. All ingredient amounts are listed as kilogram per 1000 kilogram batch of product, unless otherwise specified.

TABLE 4

| Ingredient | Ex. 2 | Ex. 3 | Ex. 4 | Ex. 5 | Ex. 6 |
| --- | --- | --- | --- | --- | --- |
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 3' sialyllactose | 0.0948 | 0.090 | 0.085 | 9.479 | 9.005 |
| Galactooligosaccharides | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 110 g | 150 g | 200 g | 250 g | 300 g |
| Nucleotide/chloride | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| Vitamin C | 130 g | 200 g | 250 g | 300 g | 350 g |
| DHA oil | 60 g | 100 g | 120 g | 150 g | 200 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin ADEK premix | 47.4 g | 47.4 g | 47.4 g | 47.4 g | 47.4 g |
| RRR-alpha tocopherol | 7 g | 20 g | 30 g | 40 g | 50 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 7-11

Examples 7-11 illustrate ready-to-feed nutritional emulsions of the present disclosure, the ingredients of which are listed in the table below. All ingredient amounts are listed as kilogram per 1000 kilogram batch of product, unless otherwise specified.

TABLE 5

| Ingredient | Ex. 7 | Ex. 8 | Ex. 9 | Ex. 10 | Ex. 11 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 6' sialylallactose | 0.0948 | 0.0901 | 0.0853 | 9.479 | 9.0047 |
| Galactooligosaccharides | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 | 448.28 g |
| Soy lecithin | 355.74 g | 355.74 g | 355.74 g | 355.74 | 355.74 g |
| Stabilizer | 355.74 g | 355.74 g | 355.74 g | 355.74 | 355.74 g |
| ARA | 110 g | 150 g | 200 g | 250 g | 300 g |
| Nucleotide/chloride | 293.26 g | 293.26 g | 293.26 g | 293.26 | 293.26 g |
| Potassium chloride | 226.45 g | 226.45 g | 226.45 g | 226.45 | 226.45 g |
| Ascorbic acid | 445.94 g | 445.94 g | 445.94 g | 445.94 | 445.94 g |
| Vitamin mineral premix | 142.88 g | 142.88 g | 142.88 g | 142.88 | 142.88 g |
| Vitamin C | 130 g | 200 g | 250 g | 300 g | 350 g |
| DHA | 60 g | 100 g | 120 g | 150 g | 200 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin ADEK premix | 47.40 g | 47.40 g | 47.40 g | 47.40 g | 47.40 g |
| RRR-alpha tocopherol | 7 g | 20 g | 30 g | 40 g | 50 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 12-16

Examples 12-16 illustrate spray dried nutritional powders of the present disclosure, the ingredients of which are listed in the table below. All ingredient amounts are listed as kilogram per 1000 kilogram batch of product, unless otherwise specified.

TABLE 6

| Ingredient | Ex. 12 | Ex. 13 | Ex. 14 | Ex. 15 | Ex. 16 |
|---|---|---|---|---|---|
| Condensed Skim Milk | 698.5 | 698.5 | 698.5 | 698.5 | 698.5 |
| Lactose | 386.0 | 386.0 | 386.0 | 386.0 | 386.0 |
| High oleic safflower oil | 114.4 | 114.4 | 114.4 | 114.4 | 114.4 |
| Soybean oil | 85.51 | 85.51 | 85.51 | 85.51 | 85.51 |
| Coconut oil | 78.76 | 78.76 | 78.76 | 78.76 | 78.76 |
| 3' sialylallactose | 0.3792 | 0.3604 | 0.3412 | 37.916 | 36.0188 |
| Galactooligosaccharides | 69.50 | 69.50 | 69.50 | 69.50 | 69.50 |
| Whey protein concentrate | 51.08 | 51.08 | 51.08 | 51.08 | 51.08 |
| Potassium citrate | 9.168 | 9.168 | 9.168 | 9.168 | 9.168 |
| Calcium carbonate | 4.054 | 4.054 | 4.054 | 4.054 | 4.054 |
| Soy lecithin | 1.120 | 1.120 | 1.120 | 1.120 | 1.120 |
| ARA | 825 g | 1125 g | 1500 g | 1875 g | 2250 g |
| Nucleotide/chloride premix | 2.347 | 2.347 | 2.347 | 2.347 | 2.347 |
| Potassium chloride | 1.295 | 1.295 | 1.295 | 1.295 | 1.295 |
| Ascorbic acid | 1.275 | 1.275 | 1.275 | 1.275 | 1.275 |
| Vitamin mineral premix | 1.116 | 1.116 | 1.116 | 1.116 | 1.116 |
| Vitamin C | 975 g | 1500 g | 1875 g | 2250 g | 2625 g |

TABLE 6-continued

| Ingredient | Ex. 12 | Ex. 13 | Ex. 14 | Ex. 15 | Ex. 16 |
|---|---|---|---|---|---|
| DHA | 60 g | 100 g | 120 g | 150 g | 200 g |
| Magnesium chloride | 1.038 | 1.038 | 1.038 | 1.038 | 1.038 |
| Sodium chloride | 579.4 g | 579.4 g | 579.4 g | 579.4 g | 579.4 g |
| Ferrous sulfate | 453.6 g | 453.6 g | 453.6 g | 453.6 g | 453.6 g |
| Choline chloride | 432.1 g | 432.1 g | 432.1 g | 432.1 g | 432.1 g |
| Vitamin ADEK premix | 377.2 g | 377.2 g | 377.2 g | 377.2 g | 377.2 g |
| RRR-alpha tocopherol | 52.5 g | 150 g | 225 g | 300 g | 375 g |
| Ascorbyl Palmitate | 361.3 g | 361.3 g | 361.3 g | 361.3 g | 361.3 g |
| Mixed carotenoid premix | 350.1 g | 350.1 g | 350.1 g | 350.1 g | 350.1 g |
| Mixed Tocopherols | 159.2 g | 159.2 g | 159.2 g | 159.2 g | 159.2 g |
| L-carnitine | 26.30 g | 26.30 g | 26.30 g | 26.30 g | 26.30 g |
| Riboflavin | 3.181 g | 3.181 g | 3.181 g | 3.181 g | 3.181 g |
| Tricalcium phosphate | 0-5.23 | 0-5.23 | 0-5.23 | 0-5.23 | 0-5.23 |
| Potassium phosphate | 0-5.23 | 0-5.23 | 0-5.23 | 0-5.23 | 0-5.23 |
| Potassium hydroxide | AN | AN | AN | AN | AN |

AN = as needed

What is claimed is:

1. A method for enhancing central nervous system development in an infant, toddler, or child, the method comprising administering to the infant, toddler, or child a nutritional composition comprising:
   i) from about 20 g/L to about 50 g/L of fat;
   ii) from about 10 g/L to about 15 g/L of protein;
   iii) from about 5 mg/L to about 100 mg/L of RRR-alpha tocopherol acetate;
   iv) less than about 8 mg/L of non-RRR-alpha-tocopherol isomers;
   v) at least about 130 mg/L of ascorbic acid;
   vi) from about 60 mg/L to about 180 mg/L of DHA, where the concentration of DHA is based on the nutritional composition; and
   vii) from about 120 mg/L to about 360 mg/L of ARA, where the concentration of ARA is based on the nutritional composition;
   wherein the DHA to RRR-alpha tocopherol acetate ratio is from about 7.5:1 to about 20:1 and the ARA to RRR-alpha tocopherol acetate ratio is from about 15:1 to about 40:1, and wherein the ratio of RRR-alpha-tocopherol acetate to non-RRR-alpha-tocopherol isomers is from 1:5 to 99:1.

2. The method of claim 1, wherein the method enhances cognitive development in the infant, toddler, or child.

3. The method of claim 1, wherein the nutritional composition comprises less than about 0.5 mg/L of the non-RRR alpha tocopherol isomers.

4. The method of claim 1, wherein the nutritional composition comprises less than about 5 mg/L of the non-RRR alpha tocopherol isomers.

5. The method of claim 1, wherein the nutritional composition further comprises one or more materials selected from a carbohydrate, one or more additional vitamins, a mineral, a carotenoid, and combinations thereof.

6. The method of claim 1, wherein the nutritional composition further comprises at least one carotenoid.

7. The method of claim 6, wherein the carotenoid is trans-lutein.

8. The method of claim 1, wherein the nutritional composition is an infant formula.

* * * * *